(12) United States Patent
Hagemann et al.

(10) Patent No.: US 7,601,658 B2
(45) Date of Patent: Oct. 13, 2009

(54) ELASTIC LAMINATE

(75) Inventors: Andreas Hagemann, Rhede (DE); Ralf Niepelt, Gronau (DE); Henner Sollmann, Bad Bentheim (DE); Georg Baldauf, Laer (DE)

(73) Assignee: Nordenia Deutschalnd Gronau GmbH, Gronau (DE)

( * ) Notice: Subject to any disclaimer, the term of this patent is extended or adjusted under 35 U.S.C. 154(b) by 0 days.

(21) Appl. No.: 11/632,925

(22) PCT Filed: Jul. 20, 2005

(86) PCT No.: PCT/EP2005/007917

§ 371 (c)(1),
(2), (4) Date: Apr. 12, 2007

(87) PCT Pub. No.: WO2006/008149

PCT Pub. Date: Jan. 26, 2006

(65) Prior Publication Data

US 2008/0038983 A1     Feb. 14, 2008

(30) Foreign Application Priority Data

Jul. 21, 2004   (DE) .................. 10 2004 035 396

(51) Int. Cl.
*D04H 1/00*       (2006.01)
*D04H 13/00*    (2006.01)
*D04H 3/00*       (2006.01)
*D04H 5/00*       (2006.01)

(52) U.S. Cl. .......... 442/328; 442/62; 442/104; 442/105; 442/381

(58) Field of Classification Search ........... 442/328, 442/381, 62, 104, 105
See application file for complete search history.

(56) References Cited

FOREIGN PATENT DOCUMENTS

| DE | 298 25 018 U1 | 2/2004 |
|---|---|---|
| EP | 1 437 112 A | 7/2004 |
| WO | WO 94/00292 A | 1/1994 |
| WO | WO 95/19258 A | 7/1995 |
| WO | WO 96/34741 A | 11/1996 |
| WO | WO 01/32403 A | 5/2001 |
| WO | WO 01/47710 A | 7/2001 |

OTHER PUBLICATIONS

International Search Report.

*Primary Examiner*—Norca L Torres-Valazquez
(74) *Attorney, Agent, or Firm*—Collard & Roe, P.C.

(57) ABSTRACT

The invention relates to an elastic laminate. The laminate is made from a co-extruded elastic film, comprising an elastomeric support layer, at least one cover layer and at least one textile outer layer made from a non-woven. The cover layer has a low layer thickness by comparison with the support layer. The outer layer is laminated onto the cover layer. According to the invention, the cover layer is made from an elastomeric material, with essentially the same expansion properties as the material of the support layer and contains additives for modification of the surface properties.

11 Claims, No Drawings

ELASTIC LAMINATE

CROSS REFERENCE TO RELATED APPLICATIONS

Applicants claim priority under 35 U.S.C. §119 of German Application No. 10 2004 035 396.4 filed Jul. 21, 2004. Applicants also claim priority under 35 U.S.C. §365 of PCT/EP2005/007917 filed Jul. 20, 2005. The international application under PCT article 21(2) was not published in English.

The invention relates to an elastic laminate, consisting of a) a co-extruded elastic film that has an elastomer support layer and at least one cover layer, and b) at least one textile outer layer made of a nonwoven, whereby the cover layer has a low layer thickness in comparison with the support layer, and the outer layer is laminated onto the cover layer. Such an elastic laminate is suitable for closure tapes and elastic edgings on baby diapers. Furthermore, elastic bandage material can be produced from the elastic laminate. Another application possibility is use as an elastic strip in caps, sports covers, and the like.

An elastic laminate having the characteristics described is known from DE 298 25 018 U1. The laminate contains a co-extruded elastic film that has an elastomer support layer and non-sticky cover layers. The cover layers consist of semi-crystalline or amorphous polymers that have less elastomer behavior than the support layer. Preferably, the cover layers are not elastic and consist of polyolefins. The cover layers, which are essentially plastically deformable, are supposed to produce good adhesion between the elastomer material of the cover layer and the textile outer layer, and are also considered to be necessary, within the framework of the prevailing teaching, so that the elastic film can be drawn off from a roll, passed to a laminating mechanism, and connected with a nonwoven layer there. However, the non-elastomer cover layers have a disadvantageous effect on the stretching behavior of the elastic laminate. They contribute to the fact that the elastic laminate does not recover completely after stretching, and demonstrates permanent elongation. The effect is all the greater the thicker and stiffer the cover layers are. Within the framework of the known measures, one therefore attempts to apply cover layers that are as thin as possible, and to compensate the negative effect of the cover layers that can stretch plastically by means of a thicker elastomer support layer. With this background, the invention is based on the task of improving the elasticity of the laminate. The elastic film that determines the stretching behavior of the laminate is supposed to have a low film thickness and recover as completely as possible after stretching.

This task is accomplished, according to the invention, in that the cover layer of the elastic film consists of an elastomer material, which possesses a marked elastic component after tensile stress at room temperature, just like the elastomer support layer, in contrast to thermoplastics, and contains additives for modifying the surface properties. No warping, microtextures, or other structures that indicate a change in the film can be determined on the surface of the film, with the unaided eye, after reversible stretching by 400%, for example. The surface of the film can be modified by means of suitable additives in the cover layers, in such a manner that the film is not sticky and can be processed well. Because of the multi-layer structure of the film, the additives are effectively concentrated in the edge zones of the elastic film. The amounts of additives for modification of the surface properties, which are small with reference to the total mass of the elastic film, do not have any effect on the stretching properties of the elastic film.

The elastomer material for the cover layer and the support layer can consist of a thermoplastic elastomer from the group of block copolymers, elastomer polyurethanes, or olefin elastomers, or also of mixtures of these elastomers with one another. Suitable block copolymers are, in particular, styrene/isoprene, butadiene, or ethylene-butylene/styrene block copolymers (SIS, SBS, or SEBS). Olefin elastomers that can be used are, for example, ethylene-propylene elastomers, ethylene-propylene-diene polymer elastomers, and metallocene-polyolefin elastomers. Elastomer compositions can furthermore also contain ethylene-vinyl acetate elastomers. The elastomer material of the cover layer can correspond to the elastomer material of the support layer.

The support layer can have a homogeneous composition, in cross-section, or also zones having different composition. In the latter case, the elasticity behavior of the support layer can be modified by means of the material composition and thickness of the zones. A support layer that consists of several zones, in cross-section, can be produced in simple manner, for example, in that a multi-layer, extruded film tube is laid together to form a flat film strip, at high temperatures, whereby the inside layers of the film tube melt together to form a core zone of the flattened film strip.

Furthermore, the support layer can contain additives for improving the adhesion capacity between support layer and cover layer. If the support layer has zones that differ with regard to their material composition, the additives are preferably contained only in the edge zones of the support layer that are adjacent to the cover layer. The cover layer preferably contains anti-blocking agents and/or lubricants as additives for modification of the surface properties. The additives are supposed to have a de-blocking effect and not make adhesion to the nonwoven significantly more difficult. Polymer additives are suitable as additives, particularly polyolefins, copolymers of polyolefins, and polystyrene. In general, polymers that are more or less compatible with the elastomer are suitable. Furthermore, inorganic fillers, particularly talcum or chalk, can be used as additives. Furthermore, anti-blocking agents, e.g. silicon dioxide, silicates, calcium carbonates, are suitable. Finally, fatty acid amides can also be used as lubricants. The stated additives can be used as the sole component or in mixtures. According to a preferred embodiment of the invention, the additives consist of polystyrene or a mixture of talcum and polypropylene, or the combination of EVA and a lubricant. The proportion of the additives in the cover layer, in terms of amount, can be established using orientation experiments. The proportion of the additives contained in the cover layer is less than 50 wt.-%, with reference to the mass of the cover layer. Preferably, the proportion of non-elastomer additives contained in the cover layer is less than 30 wt.-%, with reference to the mass of the cover layer.

The elastomer support layer can have a thickness between 20 μm and 200 μm. The thickness of the elastomer cover layer is preferably less than 20 μm.

The connection between the textile outer layer and the cover layer can be produced in different ways. A first, preferred embodiment provides that the textile outer layer is glued to the cover layer of the elastic film over its entire area. Furthermore, it lies within the scope of the invention that the textile outer layer is glued to the cover layer at point-shaped or line-shaped contact areas, or connected by means of thermo-bonding.

"Nonwoven" refers to a layer of nonwoven fabric composed of direction-oriented or randomly ordered fibers that are connected with one another by means of friction and/or cohesion and/or adhesion. The layer of nonwoven fabric can be mechanically compacted. Furthermore, the fibers can be thermally bonded, or bonded by means of a hot-melt adhesive introduced in powder form. The nonwoven material of the outer layer can consist of elastomer fibers. Another embodiment of the invention provides that the nonwoven material of the outer layer consists of elastomer fibers that demonstrate significant permanent elongation after stretching, and that the outer layer has a stretchable region that has been produced by means of crosswise stretching of the laminate in a meander-shaped roller nip between two profile rollers that engage into one another. It is practical if the stretchable region of the outer layer is dimensioned in such a manner that the laminate can be stretched by at least 100% with a stretching force of less than 4 N, with reference to a sample strip having a width of one cm.

According to a preferred embodiment of the invention, the elastic film has a support layer as well as an elastic cover layer on both sides of the support layer, and a textile outer layer of nonwoven is laminated onto both side of the elastic film, in each instance. The support layer of the elastic film can have a homogeneous composition, in cross-section, or also several zones that differ with regard to their material composition.

The invention claimed is:

1. Elastic laminate comprising a co-extruded elastic film that has an elastomer support layer and at least one cover layer, and
   at least one textile outer layer made of a nonwoven,
   whereby the cover layer has a low layer thickness in comparison with the support layer, and the outer layer is laminated onto the cover layer, wherein the cover layer comprises an elastomer material, which possesses a marked elastic component after tensile stress at room temperature, just like the elastomer support layer, in contrast to thermoplastics, and contains additives for modifying the surface properties, wherein the elastomer material for the cover layer and the support layer consists of a thermoplastic elastomer from the group of block copolymers, elastomer polyuretharies, or mixtures of these elastomers and wherein the nonwoven material of the outer layer comprises non-elastomer fibers that have a significant permanent deformation after stretching, and wherein the outer layer has a stretchable region that has been produced by means of crosswise stretching of the laminate in a meander-shaped roller nip between two profile rollers that engage into one another.

2. Elastic laminate according to claim 1, wherein the elastomer material of the cover layer corresponds to the elastomer material of the support layer.

3. Elastic laminate according to claim 1, wherein the cover layer contains additives for improving the adhesion capacity between support layer and cover layer.

4. Elastic laminate according to claim 1, wherein the cover layer contains anti-blocking agents and/or lubricants as additives for modification of the surface properties.

5. Elastic laminate according to claim 1, wherein the cover layer contains polyolef ins, copolymers of polyolefins, or polystyrene, inorganic fillers, inorganic anti-blocking agents, lubricants, or mixtures of these substances as additives.

6. Elastic laminate according to claim 5, wherein the cover layer comprises non-elastomer additives in a proportion less than 50 wt.-% with reference to the mass of the cover layer.

7. Elastic laminate according to claim 1, wherein the elastomer support layer has a thickness between 20 μm and 200 μm, and wherein the thickness of the elastomer cover layer is less than 20 μm.

8. Elastic laminate according claim 1, wherein the textile outer layer is glued to the cover layer of the elastic film over its entire area.

9. Elastic laminate according to claim 1, wherein the textile outer layer is glued to the cover layer at point-shaped or line-shaped contact surfaces, or connected by means of thermobonding.

10. Elastic laminate according to claim 1, wherein the stretchable region of the outer layer is dimensioned in such a manner that the laminate can be stretched by at least 100% with a stretching force of less than 4 N/cm.

11. Elastic laminate according to claim 1, wherein the elastic film is structured in three layers, and a textile outer layer of nonwoven is laminated onto both sides of the elastic film, in each instance.

* * * * *

UNITED STATES PATENT AND TRADEMARK OFFICE
CERTIFICATE OF CORRECTION

PATENT NO. : 7,601,658 B2
APPLICATION NO. : 11/632925
DATED : October 13, 2009
INVENTOR(S) : Hagemann et al.

Page 1 of 1

It is certified that error appears in the above-identified patent and that said Letters Patent is hereby corrected as shown below:

In Column 4, line 15, (Line 2 of Claim 5) please change "polyolef ins" to correctly read: --polyolefins--.

In Column 4, line 18, (Line 1 of Claim 6), please change "claim 5" to correctly read: --claim 4--.

Signed and Sealed this

Twenty-fourth Day of November, 2009

David J. Kappos
*Director of the United States Patent and Trademark Office*